United States Patent [19]

Schwartz, Jr.

[11] Patent Number: 4,868,316

[45] Date of Patent: Sep. 19, 1989

[54] PROCESS FOR THE PREPARATION OF DIETHER DIPHTHALIC ANHYDRIDES

[75] Inventor: Willis T. Schwartz, Jr., Grand Island, N.Y.

[73] Assignee: Occidental Chemical Corporation, Niagara Falls, N.Y.

[21] Appl. No.: 42,760

[22] Filed: Apr. 27, 1987

[51] Int. Cl.⁴ .......................................... C07D 307/89
[52] U.S. Cl. .................................................. 549/241
[58] Field of Search ......................................... 549/241

[56] References Cited

U.S. PATENT DOCUMENTS

| | | | |
|---|---|---|---|
| 3,850,964 | 11/1974 | Williams | 549/232 |
| 3,992,407 | 11/1976 | Markezich | 548/461 |
| 4,697,023 | 9/1987 | Schwartz et al. | 549/241 |
| 4,757,149 | 7/1988 | Maresca | 548/461 |

OTHER PUBLICATIONS

Bader et al., J. Am. Chem. Soc., vol. 75, (1953), p. 5416.
Blicke et al., J. Am. Chem. Soc., vol. 51 (1929), pp. 1865–1875.
Solomon, Fundamentals of Organic Chemistry, Wiley (1986), p. 552.
Fieser et al., Organic Chemistry, Heath, Boston (1965), pp. 896–897.

*Primary Examiner*—Richard L. Raymond
*Attorney, Agent, or Firm*—James F. Tao; Arthur S. Cookfair

[57] ABSTRACT

Diether diphthalic anhydrides are prepared by reacting fluorophthalic anhydride with an aromatic dihydroxyl compound in the presence of potassium fluoride and a polar, aprotic solvent.

25 Claims, No Drawings

PROCESS FOR THE PREPARATION OF DIETHER DIPHTHALIC ANHYDRIDES

BACKGROUND OF THE INVENTION

This invention relates to a method for the preparation of diphthalic anhydrides. The products are useful chemical intermediates for the further preparation of various compounds such as the corresponding tetra-carboxylic acids and the various derivatives thereof, including for example, the salts, esters, acyl halides, amides, imides and the like. The diphthalic anhydrides are particularly useful as monomers in the preparation of polyimides, for example by polycondensation with a suitable diamine, such as ethylenediamine or phenylenediamine.

Various methods for the preparation of diether diphthalic anhydrides have been described in the chemical literature. Earlier preparations were directed to the formation of the diether di-o-xylyl groups followed by oxidation to the diether diphthalic anhydride. See Koton et al, Zh. Org. Khim. 4, 774 (1968); and Zh. Org. Khim. 6, 88 (1970).

U.S. Pat. No. 3,965,125 to Myers teaches the preparation of halogenated phthalimides from halogenated phthalic anhydride and reaction of the phthalimide with an alkaline metal salt of a phenol or a diphenol to form the bis-ether imide which is then hydrolyzed, acidified, and dehydrated to the bis-ether phthalic anhydride.

Heath et al (U.S. Pat. No. 3,956,320) disclose the preparation of aromatic bis(ether anhydride) by reaction of a nitro-substituted phenyl dinitrile with a metal salt of a dihydroxy aryl compound in the absence of a dipolar aprotic solvent and conversion of the resultant aryl-oxy tetranitrile to the tetra-acid followed by dehydration to the aryloxy dianhydride. Thus, for example, the patentees disclose the reaction of hydroquinone with 4-nitrophthalolnitrile in the presence of potassium carbonate, followed by hydrolysis, acidification and dehydration to form the hydroquinone di-ether phthalic anhydride.

Johnson et al (U.S. Pat. No. 4,020,069) teach the reaction of a 4-nitro-N-alkyl phthalimide and an aromatic dihydroxy compound in the presence of potassium carbonate and dimethyl sulfoxide followed by hydrolysis to form a bis-ether dicarboxylic acid which may then be dehydrated to form the aromatic ether dianhydride.

U.S. Pat. No. 3,850,964 to Williams discloses a method for making aromatic bis(ether anhydrides) by reaction of alkali metal diphenoxides with halo or nitro-substituted aromatic anhydrides. Thus, for example, a sodium salt of 2,2-bis-(4-hydroxyphenyl)propane was reacted with 3-fluorophthalic anhydride in anhydrous dimethyl formamide to form 2,2-bis[4-(2,3-dicarboxyphenoxy)phenyl]propane dianhydride.

Markezich (U.S. Pat. No. 3,992,407) discloses the preparation of aromatic bisimides by reaction of a 3- or 4-fluoro-N-substituted phthalimide with an aromatic dihydroxy compound in the presence of a solid alkali metal fluoride, such as potassium fluoride, and using a dipolar aprotic compound as a solvent. Markezich discloses the preparation of aromatic bisimides by reaction of a 3- or 4-nitro-N-substituted phthalimide with an aromatic dihydroxy compound in the presence of a solid alkali metal fluoride in a dipolar aprotic solvent.

SUMMARY OF THE INVENTION

In accordance with the present invention there is provided a process for the preparation of diether diphthalic anhydrides of the formula

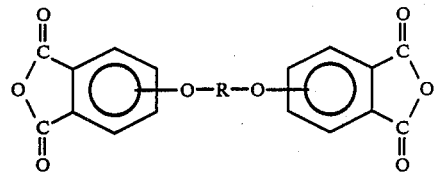

wherein R is selected from the group consisting of

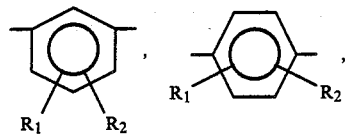

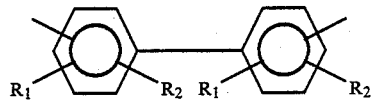

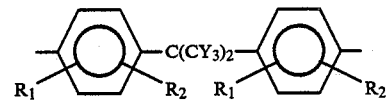

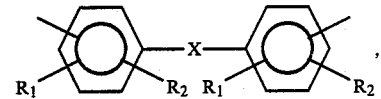

where $R_1$ and $R_2$ are independently selected from the group consisting of -phenyl, -phenoxy, —H, —CF$_3$, —CH$_3$, —OCH$_3$, —NO$_2$, —CN and —F; Y is —H or —F; and X is selected from the group consisting of —(CH$_2$)$_n$—,

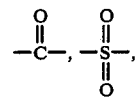

—O— and —S—; and n is a whole number from 1 to 5; which comprises reacting a fluorophthalic anhydride of the formula

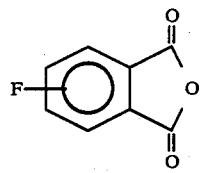

with an aromatic dihydroxyl compound of the formula HO—R—OH where R is as defined above, in the presence of potassium fluoride or cesium fluoride or a mixture thereof, and a polar aprotic solvent.

Among the dihydroxyl compounds that may be employed in the process of the invention are included: hydroquinone;

resorcinol;
3,4'-dihydroxydiphenylmethane;
4,4'-dihydroxybenzophenone;
4,4'-dihydroxydiphenyl ether;
2,2-bis-(2-hydroxyphenyl)propane;
2,4'-dihydroxydiphenylmethane;
bis-(2-hydroxyphenyl)methane;
2,2-bis-(4-hydroxyphenyl)propane (i.e., bisphenol-A);
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3',5,5'-tetramethylbiphenyl;
2,4'-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide; and the like.

The proportions of fluorophthalic anhydride and dihydroxyl compound may vary considerably. However, it is preferred to employ a molar ratio of fluorophthalic anhydride: dihydroxyl compound of at least about 2:1 and most preferably about 2.1-2.3:1. Higher ratios may be employed but generally provide no special advantage and may be uneconomical since the fluorophthalic anhydride is generally the more expensive reactant.

The fluorophthalic anhydride reactant may be either 3-fluoro- or 4-fluorophthalic anhydride or a mixture thereof and may be provided as an initial component of the reaction mixture or may be formed in-situ by the reaction of a bromo-, chloro-, or iodo-phthalic anhydride with KF. In the process of the invention, the fluorine atom on the fluorophthalic anhydride reactant functions as a leaving group and becomes the site for the formation of the ether bridge.

The process of the invention is preferably carried out at atmospheric pressure, but super-atmospheric pressure, for example under autogeneous conditions may be employed, if desired. The process is preferably carried out in the presence of a polar, aprotic solvent such as N-methyl-pyrrolidone, dimethyl formamide, dimethyl acetamide, triglyme, sulfolane, or the like. The preferred solvent is sulfolane.

The temperature at which the process is carried out may vary considerably, but will generally be within the range of about 120° to about 220° Celsius. Higher or lower temperatures may be employed but are less efficient. The choice of solvent may govern the temperature employed. For example, at atmospheric conditions the boiling point of the solvent becomes a limiting condition. The preferred temperature is in the range of about 160°-210°, and most preferably, about 170°-190° Celsius. Sulfolane is a particularly useful solvent for this preferred temperature range.

The proportions of reactants may vary considerably, however, it is preferred that the alkali metal fluoride be employed in sufficient proportions to provide about one equivalent of potassium (or cesium) per mole of fluorophthalic anhydride. In the reaction, the alkali metal fluoride functions as a hydrogen fluoride acceptor. When the fluorophthalic anhydride reactant is to be formed in-situ from an initial mixture of chlorophthalic anhydride, bromophthalic anhydride or iodophthalic anhydride, it is preferred to provide at least about two equivalents of alkali metal fluoride per mole of chloro- or bromo- or iodophthalic anhydride. Preferably the alkali metal compound is employed in substantial excess, for example, up to about 50 percent excess, of the aforesaid equivalent proportions.

The following examples are provided to further illustrate this invention and the manner in which it may be carried out. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

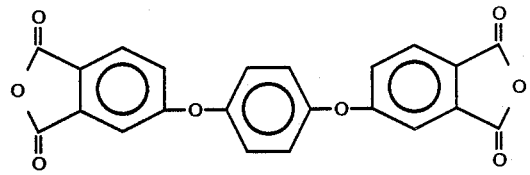

A mixture of 11.0 parts (0.1 mole) of hydroquinone, 36.5 parts (0.22 mole) of 4-fluorophthalic anhydride, and 18.0 parts (0.5 mole) of anhydrous potassium fluoride, in 126 parts of sulfolane was heated to about 180° C. and maintained thereat, with stirring for about one hour. The reaction mixture was cooled to room temperature and washed with water to remove sulfolane. The solid residue was dried, dissolved in dimethyl formamide and analyzed by liquid chromatography. The product (based on area percent) consisted of 0.5 percent 4-fluorophthalic anhydride, 2.6 percent hydroquinone, and 92.7 percent hydroquinone-bis(4-phthalic anhydride) diether.

EXAMPLE 2

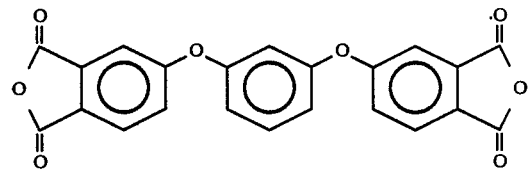

The procedure of Example 1 was repeated except that resorcinol was substituted for the hydroquinone. Analysis of the reaction product by liquid chromatographic techniques indicated, in area percent, 82.8 percent resorcinol-bis(4-phthalic anhydride) diether.

EXAMPLE 3

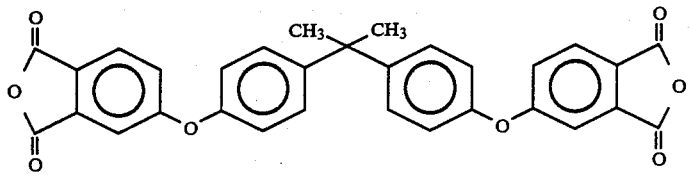

To a solution of 42.7 parts (0.25 mole) of 4-fluorophthalic anhydride in 117 parts of sulfolane was added 27.4 parts (0.12 mole) of bisphenol-A and 15.7 parts (0.27 mole) of dried potassium fluoride. This mixture was heated at 180°–185° C., with stirring, for 3 hours. HPLC analysis of the reaction mixture showed the absence of starting material and a major product component consisting of 87.5% of the reaction mixture. Mass spectral analysis confirmed the identity of this component as the desired bisphenol-A diphthalic anhydride (as set forth in the structural formula above). The HPLC retention time was also the same as that found with a known sample of the desired dianhydride.

EXAMPLE 4

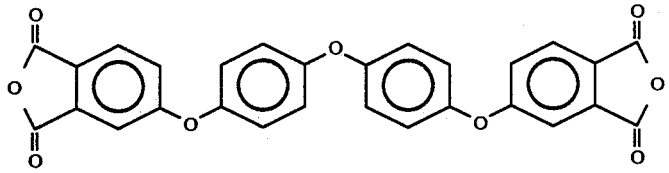

To a solution of 0.429 parts (0.002 mole) of 4,4'-dihydroxybenzophenone and 0.787 parts (0.005 mole) of 4-fluorophthalic anhydride in 3.6 parts of sulfolane, was added 0.25 parts (0.004 mole) of dried potassium fluoride. The resultant mixture was heated to about 175° C. and maintained thereat, with stirring, for about 3¾ hours. Analysis of the reaction mixture by HPLC/MS showed 79.7% (by area) of desired product. (Confirmation by mass spec.)

EXAMPLE 5

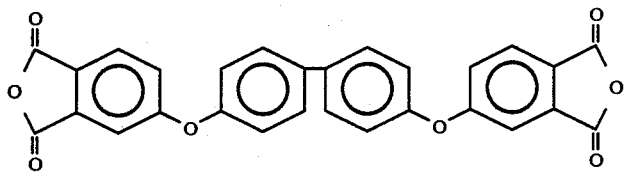

Dried potassium fluoride (0.25 parts; 0.004 mole) was added to a solution of 0.8 parts (0.006 mole) of 4-fluorophthalic anhydride and 0.37 parts (0.002 mole) of 4,4'-biphenol dissolved in approximately 3.5 parts of sulfolane. After stirring for 3¾ hours at 175° C., the mixture was analyzed by HPLC/MS and found to contain 77.6 area percent of 4,4'-biphenol diphthalic anhydride.

What is claimed is:

1. A process for the preparation of diether diphthalic anhydrides of the formula

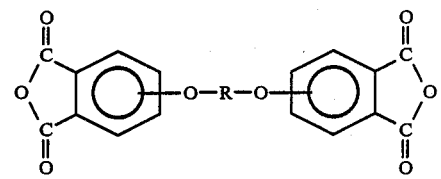

wherein R is selected from the group consisting of

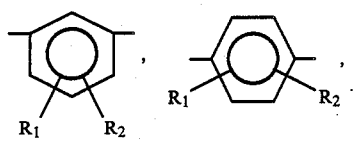

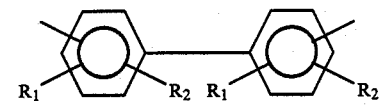

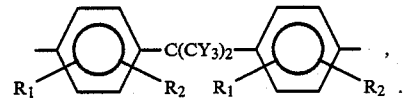

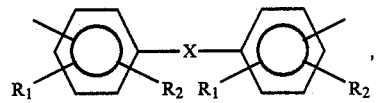

where $R_1$ and $R_2$ are independently selected from the group consisting of -phenyl, -phenoxy, —H, —$CF_3$, —$CH_3$, —$OCH_3$, —$NO_2$, —CN and —F; Y is —H or —F; and X is selected from the group consisting of —$(CH_2)_n$—,

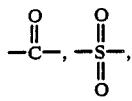

—O— and —S—; and n is a whole number from 1 to 5; which comprises reacting a fluorophthalic anhydride of the formula

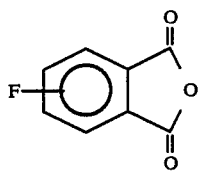

with an aromatic dihydroxyl compound of the formula HO—R—OH where R is as defined above, in the presence of potassium fluoride or cesium fluoride or a mixture thereof, and a polar aprotic solvent.

2. A process according to claim 1 carried out at a temperature of about 120° to about 220° Celsius.

3. A process according to claim 2 wherein the alkali metal fluoride is potassium fluoride.

4. A process according to claim 2 wherein the alkali metal fluoride is cesium fluoride.

5. A process according to claim 1 wherein the fluorophthalic anhydride is 4-fluorophthalic anhydride.

6. A process according to claim 5 wherein the alkali metal fluoride is potassium fluoride.

7. A process according to claim 6 carried out at a temperature of about 120° to about 220° Celsius.

8. A process according to claim 7 carried out at a temperature of about 160° to about 210° Celsius.

9. A process according to claim 8 wherein the solvent is sulfolane.

10. A process according to claim 1 wherein the fluorophthalic anhydride is 3-fluorophthalic anhydride.

11. A process according to claim 5 wherein the aromatic dihydroxyl compound is hydroquinone.

12. A process according to claim 5 wherein the aromatic dihydroxyl compound is resorcinol.

13. A process according to claim 5 wherein the aromatic dihydroxyl compound is 2,2-bis(4-hydroxyphenyl)propane.

14. A process according to claim 5 wherein the aromatic dihydroxyl compound is 4,4'-dihydroxybenzophenone.

15. A process according to claim 5 wherein the aromatic dihydroxyl compound is 4,4'-biphenol.

16. A process according to claim 1 wherein the fluorophthalic anhydride is formed in-situ by the reaction of a halophthalic anhydride selected from the group consisting of chlorophthalic anhydride, bromophthalic anhydride, and iodophthalic anhydride with an alkali metal fluoride; and the initial amount of alkali metal fluoride is sufficient to provide at least about 2 equivalents of alkali metal per mole of halophthalic anhydride.

17. A process according to claim 16 wherein the fluorophthalic anhydride is formed in-situ by the reaction of chlorophthalic anhydride with potassium fluoride.

18. A process according to claim 16 wherein the fluorophthalic anhydride is formed in-situ by the reaction of bromophthalic anhydride with potassium fluoride.

19. A process for the preparation of a diether diphthalic anhydride which comprises reacting 4-fluorophthalic anhydride with an aromatic dihydroxyl compound selected from the group consisting of hydroquinone; resorcinol; 2,2-bis-(4-hydroxyphenyl) propane; 4,4'-dihydroxybenzophenone; and 4,4'-biphenol; in the presence of potassium fluoride and a polar aprotic solvent, at a temperature of about 160° to about 210° Celsius.

20. A process according to claim 19 wherein the solvent is sulfolane.

21. A process according to claim 20 wherein the aromatic dihydroxyl compound is hydroquinone.

22. A process according to claim 20 wherein the aromatic dihydroxyl compound is resorcinol.

23. A process according to claim 20 wherein the aromatic dihydroxyl compound is 2,2-bis-(4-hydroxyphenyl)-propane.

24. A process according to claim 20 wherein the aromatic dihydroxyl compound is 4,4'-dihydroxybenzophenone.

25. A process according to claim 20 wherein the aromatic dihydroxyl compound is 4,4'-biphenol.

* * * * *